(12) United States Patent
Speece, Jr. et al.

(10) Patent No.: US 6,740,358 B2
(45) Date of Patent: May 25, 2004

(54) REACTIVE COALESCENTS

(75) Inventors: David Gerald Speece, Jr., Reading, PA (US); Michael Damian Bowe, Newtown, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/185,632

(22) Filed: Jun. 28, 2002

(65) Prior Publication Data

US 2002/0197407 A1 Dec. 26, 2002

Related U.S. Application Data

(62) Division of application No. 09/047,547, filed on Mar. 25, 1998, now Pat. No. 6,451,380.
(60) Provisional application No. 60/042,725, filed on Apr. 8, 1997.

(51) Int. Cl.$^7$ ............................. B05D 3/02; C07C 69/74
(52) U.S. Cl. .................... 427/372.2; 560/117; 568/606
(58) Field of Search ....................... 427/372.2; 560/117; 568/606

(56) References Cited

U.S. PATENT DOCUMENTS

| | | | | |
|---|---|---|---|---|
| 2,795,564 A | * | 6/1957 | Conn et al. ................. | 524/762 |
| 4,097,677 A | | 6/1978 | Emmons et al. | |
| 4,141,868 A | * | 2/1979 | Emmons et al. ............ | 524/237 |
| 4,145,503 A | | 3/1979 | Emmons et al. | |
| 4,261,872 A | | 4/1981 | Emmons et al. | |
| 4,311,624 A | | 1/1982 | Emmons et al. | |
| 4,387,190 A | | 6/1983 | Feely | |
| 4,973,624 A | * | 11/1990 | Ohtani et al. ................. | 525/7.1 |
| 5,283,360 A | * | 2/1994 | Caubere et al. ............. | 562/220 |
| 5,346,954 A | * | 9/1994 | Wu et al. ..................... | 525/85 |
| 5,349,026 A | | 9/1994 | Emmons et al. | |
| 5,510,516 A | * | 4/1996 | Caubere et al. ............. | 560/220 |
| 5,565,535 A | * | 10/1996 | Costin et al. ............... | 526/240 |
| 5,710,227 A | | 1/1998 | Freeman et al. | |

* cited by examiner

Primary Examiner—Ceila Chang
Assistant Examiner—Taylor V Oh
(74) Attorney, Agent, or Firm—Gary D. Greenblatt

(57) ABSTRACT

Compounds useful as reactive coalescents and methods of improving the stability of reactive coalescents are disclosed. A process for the preparation of low molecular weight polymers which are also useful as reactive coalescents is also disclosed.

6 Claims, No Drawings

REACTIVE COALESCENTS

This is a divisional of application Ser. No. 09/047,547, filed Mar. 25, 1998, now U.S. Pat. No. 6,451,380, which claims priority to provisional application 60/042,725, filed Apr. 8, 1997.

This invention relates to compounds which are useful as reactive coalescents, methods of improving the stability of reactive coalescents, and a process of preparing low molecular weight polymers which are useful as reactive coalescents.

Water based polymers having a low glass transition temperature ("Tg") can be formulated into coatings without plasticizers. These coatings often have inadequate hardness for many applications. Many applications, such as gloss and semigloss paint formulations, require the properties of a hard polymer, i.e. a polymer with a Tg significantly above the ambient temperature. To meet these needs, a volatile coalescent or plasticizer is typically used to achieve film formation. The use of these volatile solvents in coatings is coming under scrutiny due to pollution and odor problems.

Attempts have been made to use "reactive coalescents". Reactive coalescents are compounds which aid in film formation similar to the conventional coalescent but are non-volatile and react to become part of the final coating.

U.S. Pat. No. 4,141,868 discloses the use of dicyclopentenyloxyethyl methacrylate ("DCPOEMA") as a reactive coalescent. Vinyl reactive coalescents are reactive coalescents which contain a vinyl group. DCPOEMA, dicyclopentenyloxyethyl acrylate ("DCPOEA"), dicyclopentenyloxy acrylate ("DCPOA"), and dicyclopentenyloxy methacrylate ("DCPOMA") are examples of vinyl reactive coalescents.

Despite the disclosure, there is a continuing need for stable reactive coalescents for use in coating compositions.

We have surprisingly found that stable reactive coalescents for use in coating compositions can be obtained by altering the structure of the reactive coalescent or adding an inhibitor to the reactive coalescent.

In a first aspect, the present invention provides compounds of formula I:

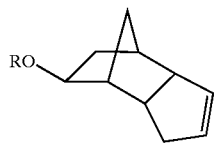
(I)

Wherein:
R=—$(CH_2)_nR^1$, —$(CH_2)_2O(CH_2)_2OH$, —$(CH_2CH_2O)_2$ $(CH_2)_3OH$, —$CH_2CH_2OCOR^2$, —$(CH_2)_2O(CH_2)_2O$ $(CH_2)_3CH_3$, —$CH_2CH(CH_3)$—OH, —$CH_2CH_2OCO$ $(CH_2)_4COOR^3$, dicyclopentenyloxyethane;

$R^1$ is selected from H, OH and $CH_3$;

$R^2$=$(C_1-C_6)$ straight chain or branched alkyl;

$R^3$ is selected from $CH_3$ and dicyclopentenyloxyethane; and n=2 to 10.

In a second aspect, the present invention provides a process for the preparation of polymers comprising:
providing a compound selected from the group consisting of DCPOEA, DCPOEMA, DCPOA, and DCPOMA;
providing a solvent selected from the group consisting of water, acetone, methanol, isopropanol, propionic acid, acetic acid, toluene, hexane, ethyl acetate, methylethyl ketone, dimethyl formamide, dimethylsulfoxide, and combinations thereof,
providing an initiator;
forming a reaction mixture by admixing the compound selected from the group consisting of DCPOEA, DCPOEMA, DCPOA, and DCPOMA, the solvent, and the initiator; and
passing the reaction mixture through a heated zone wherein the reaction mixture is maintained at a temperature of at least 175° C. for from 0.1 seconds to 300 seconds to form a liquid polymer with a number average molecular weight of from 450 to 10,000.

In a third aspect, the present invention provides a method of use comprising:
providing an emulsion polymer;
providing a liquid polymer prepared from a compound selected from the group consisting of DCPOEA, DCPOEMA, DCPOA, and DCPOMA, the liquid polymer having a number average molecular weight of from 450 to 10,000;
forming a coating composition by admixing the liquid polymer having a number average molecular weight of from 450 to 10,000 with the emulsion polymer; and;
applying said coating composition to a substrate wherein the coating composition forms a continuous film on the substrate.

In another embodiment, the present invention provides a composition comprising:
from 1% to 25% of a vinyl reactive coalescent based on a weight reactive coalescent to total weight of composition basis;
from 1 ppm to 10,000 ppm of an inhibitor selected from the group consisting of 4-methoxyphenol, 2,2,6,6-tetramethyl-1-piperidinyloxy, 4-oxo-2,2,6,6-tetramethyl-1-piperidinyloxy, and di-tertiary butyl nitroxyl, based on a weight inhibitor to total weight of composition basis; and
from 74% to 99% of an emulsion polymer based on a weight emulsion polymer to total weight of composition basis.

In another embodiment, the present invention provides a method for improving the stability of a vinyl reactive coalescent comprising:
providing an emulsion polymer;
passing the emulsion polymer through a diafiltration apparatus; and
charging the emulsion polymer which has been passed through the diafiltration apparatus with a vinyl reactive coalescent.

In another embodiment, the present invention provides a coating composition comprising:
an emulsion polymer; and
a compound selected from the compounds of Formula I

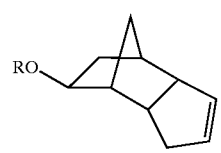
(I)

Wherein:
R=—$(CH_2)_nR^1$, —$(CH_2)_2O(CH_2)_2OH$, —$(CH_2CH_2O)_2$ $(CH_2)_3OH$, —$CH_2CH_2OCOR^2$, —$(CH_2)_2O(CH_2)_2O$ $(CH_2)_3CH_3$, —$CH_2CH(CH_3)$—OH, —$CH_2CH_2OCO$ $(CH_2)_4COOR^3$, dicyclopentenyloxyethane;

$R^1$ is selected from H, OH and $CH_3$,
$R^2=(C_1-C_6)$ straight chain or branched alkyl;
$R^3$ is selected from $CH_3$ and dicyclopentenyloxyethane; and n=2 to 10, and a liquid polymer prepared from a compound selected from the group consisting of DCPOEA, DCPOEMA, DCPOA, and DCPOMA, the liquid polymer having a number average molecular weight of from 450 to 10,000.

The inhibitors useful in this invention include hydroquinone ("HQ"), 4-methoxyphenol ("MEHQ"), phenothiazine ("PTZ"), 2,2,6,6-tetramethyl-1-piperidinyloxy ("4-HT"), and 4-oxo-2,2,6,6-tetramethyl-1-piperidinyloxy, are available from Aldrich Chemical Company. Di-tertiary butyl nitroxyl is available from Nova Molecular Technologies, Lake Geneva, Wis. The inhibitors are typically used at levels of from 1 ppm to 10,000 ppm on a weight inhibitor to total weight of the composition basis. Preferred are inhibitor levels of from 100 ppm to 1,000 ppm. More preferred are inhibitor levels of from 200 ppm to 700 ppm.

The reactive coalescents of this invention are prepared by processes known in the art. For example, direct esterification, transesterification or the use of acid halides may be employed to convert alcohols to esters of this invention. Examples of compounds of Formula I include, but are not limited to: dicyclopentenyloxyethyl acetate, dicyclopentenyloxyethyl butyrate, dicyclopentenyloxy-2-(2-hydroxyethoxy)ethane, dicyclopentenyloxy-2-(2-butoxyethoxy)ethane, dicyclopentenyloxyhexanol, dicyclopentenyloxyhexane, dicyclopentenyloxybutane, dicyclopentenyloxy (2-methyl)propane, and 1,2-bis (dicyclopentenyloxy)ethane.

The low molecular weight polymers of this invention may be useful as reactive coalescents, and may be prepared by conventional techniques, such as solution or emulsion polymerization, which are well known in the art. The low molecular weight polymers may also be prepared by the high temperature, low residence time process of this invention. In the process of this invention, a reaction mixture is formed by combining at least one compound selected from DCPOEA, DCPOEMA, DCPOA, and DCPOMA and optionally, compatible monomers with a solvent and an initiator. Suitable solvents include, but are not limited to water, acetone, methanol, isopropanol, propionic acid, acetic acid, toluene, alkanes such as hexane; esters such as ethyl acetate; methylethyl ketone, dimethyl formamide, dimethylsulfoxide, and combinations thereof. The process of this invention may be run in the absence of solvent.

Initiators are compounds which initiate the polymerization of monomers. Suitable initiators for the present invention are any conventional initiators. Among the suitable initiators that may be used are thermal free-radical initiators, such as hydrogen peroxide, certain alkyl hydroperoxides, dialkyl peroxides, persulfates, peresters, percarbonates, ketone peroxides and azo initiators. Specific free-radical initiators include, for example, hydrogen peroxide, tert-butyl hydroperoxide, di-tert-butyl peroxide, ammonium persulfate, potassium persulfate, sodium persulfate, tert-amyl hydroperoxide and methyl ethyl ketone peroxide. The free-radical initiators are typically used in amounts of 0.5 to 25% based on the total monomer weight.

Redox initiator systems may also be used. Redox initiator systems include reducing agents, for example, sodium bisulfite, sodium sulfite, hypophosphites, phosphites, isoascorbic acid, sodium formaldehyde-sulfoxylate and hydroxylamines, used in conjunction with suitable oxidizing agents, such as the thermal free-radical initiators noted above. The redox initiator systems are typically used in amounts from 0.05 to 10%, preferably from 0.5 to 5%, based on the weight of total monomer. Combinations of initiators may be used.

The process of this invention is typically run at a temperature of from 175° C. to 500° C. Preferred is a temperature of from 225° C. to 450° C. It is preferred to conduct the polymerization at a pressure of from 1,000 to 5,000 pounds per square inch ("psi"), and more preferably at from 3,200 to 4,200 psi. By low molecular weight polymers is meant polymers typically with number average molecular weights from 450 to 10,000. Preferred are polymers with number average molecular weights from 450 to 5,000. More preferred are polymers with number average molecular weights from 450 to 3,000.

Compatible monomers are monomers which are miscible with DCPOEA, DCPOEMA, DCPOA or DCPOMA. Compatible monomers include, but are not limited to: methyl acrylate, ethyl acrylate, butyl acrylate, t-butylaminoethyl methacrylate, dimethylaminoethyl methacrylate, isobornyl methacrylate, styrene, vinyl toluene, methacrylic acid, methyl methacrylate, butyl methacrylate, isobutyl methacrylate, allyl methacrylate, lauryl methacrylate, and 2-ethylhexyl methacrylate.

The reactive coalescents are typically used at levels of from 1% to 25% on a weight reactive coalescent to total weight of composition basis. Preferred are reactive coalescent levels of from 2% to 20%. More preferred are reactive coalescent levels of from 5% to 15%.

This invention may be applied to any emulsion polymer. The preparation of emulsion polymers is known in the art, see for example U.S. Pat. No. 5,346,954.

The following is a list of products used within this invention and their sources:

| Product | Source |
| --- | --- |
| Tamol ® 165 | Rohm and Haas Company |
| Triton ® CF-10 | Union Carbide |
| Drew ® ZV-22 | Ashland Chemical Company |
| RM-2020NPR | Rohm and Haas Company |
| Ti-Pure ® R-706 | DuPont Chemical Company |
| Rhoplex ® EXP-3361 | Rohm and Haas Company |
| Scotch ® Tape | Minnesota Mining and Manufacturing Company |
| Tamol ® 731 | Rohm and Haas Company |
| BYK-22 | BYK-Chemie GmbH |
| GR-7M | Union Carbide |
| Triton ® XN-45S | Union Carbide |

The following examples are intended to demonstrate the compounds and compositions of this invention and their use as stable reactive coalescents.

EXAMPLE 1
Improved Stability of DCPOEMA

Reactive coalescents containing unsaturated vinyl groups can polymerize in the can due to residual impurities in the polymer. The poor stability of the coalescent manifests itself as loss of film forming properties of the formulated coating over time. DCPOEMA is a reactive coalescent which contains 100 ppm hydroquinone as purchased. Various inhibitor types and levels were added to DCPOEMA prior to use in a coating composition. The reactive coalescent and inhibitor mixtures were prepared prior to the compositions by adding DCPOEMA to a fixed amount of solid grade inhibitor. The mixtures were then post-added to a portion of a master mix of paint 1. A portion of each sample was stored at 140° F. for 10 days. The minimum film forming temperature ("MFFT") was measured for each sample. If the DCPOEMA was stable, the MFFT remained low when compared to the control sample. If the DCPOEMA was unstable, the MFFT was elevated when compared to the control. The DCPOEMA was considered to be stable if the MFFT increased less than 5° C. after the sample was stored at 140° F. for 10 days. The results of the tests are shown in Table 1.

Paint 1

A master paint formulation containing no coalescent was prepared as follows:

18 g water, 1.61 g Tamol®165, 0.50 g Triton®CF-10, 0.25 g Drew®ZV-22, 3.75 g RM-2020NPR, and 45.0 g Ti-Pure®R-706 were ground with a high speed disperser for 15 minutes. To the mixture was added 131.27 g EXP-3361, 0.25 g Drew®ZV-22, 1.18 g RM2020NPR, and 40.25 g water with further mixing.

Sample 1 was a control sample of Paint 1 with DCPOEMA, but no additional inhibitor.

Sample 2 was prepared by combining 7.55 g of a mixture of 0.29 g of solid grade 4-HT dissolved in 57.71 g of DCPOEMA with 244.06 g of paint 1.

Sample 3 was prepared by combining 7.55 g of a mixture of 0.60 g of solid grade 4-HT dissolved in 59.40 g of DCPOEMA with 244.06 g of paint 1.

Sample 4 was prepared by combining 7.55 g of a mixture of 1.20 g of solid grade 4-HT dissolved in 58.80 g of DCPOEMA with 244.06 g of paint 1.

Sample 5 was prepared by combining 7.55 g of a mixture of 2.37 g of solid grade 4-HT dissolved in 56.88 g of DCPOEMA with 244.06 g of paint 1.

Sample 6 was prepared by combining 7.55 g of a mixture of 0.30 g of MEHQ dissolved in 59.70 g of DCPOEMA with 244.06 g of paint 1.

Sample 7 was prepared by combining 7.55 g of a mixture of 0.60 g of MEHQ dissolved in 59.40 g of DCPOEMA with 244.06 g of paint 1.

Sample 8 was prepared by combining 7.55 g of a mixture of 1.16 g of MEHQ dissolved in 56.84 g of DCPOEMA with 244.06 g of paint 1.

Sample 9 was prepared by combining 7.55 g of a mixture of 2.42 g of MEHQ dissolved in 58.08 g of DCPOEMA with 244.06 g of paint 1.

Sample 10 was prepared by combining 7.55 g of a mixture of 0.24 g of HQ dissolved in 57.71 g of DCPOEMA with 244.06 of paint 1.

Sample 11 was prepared by combining 7.55 g of a mixture of 0.60 g of HQ dissolved in 59.40 g of DCPOEMA with 244.06 g of paint 1.

Sample 12 was prepared by combining 7.55 g of a mixture of 1.19 g of HQ dissolved in 58.31 g of DCPOEMA with 244.06 g of paint 1.

Sample 13 was prepared by combining 7.55 g of a mixture of 0.31 g of PTZ dissolved in 61.69 g of DCPOEMA with 244.06 g of paint 1.

Sample 14 was prepared by combining 7.55 g of a mixture of 0.61 g of PTZ dissolved in 60.39 g of DCPOEMA with 244.06 g of paint 1.

Sample 15 was prepared by combining 7.55 g of a mixture of 1.21 g of PTZ dissolved in 59.29 g of DCPOEMA with 244.06 of paint 1.

The MFFT Test was Performed as Follows

Scotch®Tape biaxially oriented polypropylene was placed on an ICI Sheen MFFT Bar SS-3300. Samples were drawn down over the tape using a 1 inch cube Sheen Film Applicator with a gap size of 75 micron. After 60 to 90 minutes, the MFFT was read as the point where the film becomes continuous and not cracked.

The Low Temperature Film Formation Test was Performed as Follows

Samples were painted by brush onto white pine boards. The paint was applied in strips perpendicular to the length of the board. Each sample was weighed to provide a spread rate of 41.8 m$^2$/liter. The painted boards were dried for 24 hours at 40° F./70% relative humidity. A magnifying glass was used to determine the degree of cracking in the paint film. The degree of cracking was reported according to the following scale:

10=none, 9=trace, 8=trace/slight, 7=slight, 6=slight/moderate, 5=moderate, 4=moderate/heavy, 3=heavy, 2=heavy/very heavy, 1=very heavy.

A score of 10 is considered to be passing.

TABLE 1

| Sample | Inhibitor | Inhibitor Level | MFFT (° C.) Initial | MFFT (° C.) 10 Days@140F |
|---|---|---|---|---|
| 1 | None | None | 5.1 | >18 |
| 2 | 4-HT | 625 ppm | 5.1 | 5.6 |
| 3 | 4-HT | 1250 ppm | 5.3 | 5.6 |
| 4 | 4-HT | 2500 ppm | 5.3 | 5.6 |
| 5 | 4-HT | 5000 ppm | 5.3 | 5.6 |
| 6 | MEHQ | 625 ppm | 4.9 | 5.6 |
| 7 | MEHQ | 1250 ppm | 4.9 | 6.4 |
| 8 | MEHQ | 2500 ppm | 4.9 | 7.6 |
| 9 | MEHQ | 5000 ppm | 4.5 | 7.6 |
| 10 | HQ | 625 ppm | 7.8 | >18 |
| 11 | HQ | 1250 ppm | 8.0 | >18 |
| 12 | HQ | 2500 ppm | 9.2 | >18 |
| 13 | PTZ | 625 ppm | 8.0 | >18 |
| 14 | PTZ | 1250 ppm | 7.8 | >18 |
| 15 | PTZ | 2500 ppm | 9.2 | >18 |

The results demonstrate that 4-HT and MEHQ improve the stability of DCPOEMA. HQ and PTZ did not improve the stability of DCPOEMA.

EXAMPLE 2

The Level of Inhibitor Required to Stabilze DCPOEMA

The level of 4-HT required to provide stability in commercial polymers was evaluated. Samples were prepared by adding 4-HT to latex, this was called a modified latex. The modified latex was then formulated into paints. Sub-samples of Samples 16–19 were stored at 140° F. for 30 days. Sub-samples of Samples 20–23 were stored at 140° F. for 10 days. The MFFT was measured for each Sample. The results are shown in Tables 2 and 3.

Paint 2

Paint 2 was prepared for Samples 16–19 as follows:

72 g water, 12 g Tamol®731, 2 g Triton®CF-10, 2 g BYK 22, 20 g RM-2020NPR, and 300 g Ti-Pure®R-706 were ground with a high speed disperser for 15 minutes. To the mixture was added 106.32 g water, 2 g GR-7M, 544.14 g modified Rhoplex®AC-261, 26.84 g DCPOEMA, 2 g BYK-22, and 10 g water with further mixing.

Paint 3

Paint 3 was prepared for Samples 20–23 as follows:

72 g water, 12 g Tamol®731, 2 g Triton®CF-10, 2 g BYK 22, 20 g RM-2020NPR, and 300 g Ti-Pure®R-706 were ground with a high speed disperser for 15 minutes. To the mixture was added 106.32 g water, 2 g GR-7M, 544.14 g modified Rhoplex®EXP-3361, 26.84 g DCPOEMA, 2 g BYK-22, and 10 g water with further mixing.

Sample 16 was a control paint 2 with DCPOEMA, but no additional inhibitor.
Sample 17 was prepared by combining 3.84 g of a 5% aqueous 4-HT mixture with 961.85 g of paint 2.
Sample 18 was prepared by combining 7.68 g of a 5% aqueous 4-HT mixture with 961.85 g of paint 2.
Sample 19 was prepared by combining 11.50 g of a 5% aqueous 4-HT mixture with 961.85 g of paint 2.
Sample 20 was prepared by combining 20.24 g of a 5% aqueous 4-HT mixture with 2,929.60 g of paint 3.
Sample 21 was prepared by combining 26.99 g of a 5% aqueous 4-HT mixture with 2,946.35 g of paint 3.
Sample 22 was prepared by combining 43.50 g of a 5% aqueous 4-HT mixture with 2,949.10 g of paint 3.
Sample 23 was prepared by combining 58.10 g of a 5% aqueous 4-HT mixture with 2,963.70 g of paint 3.

TABLE 2

| Sample | 4-HT Level | Low Temperature Film Formation | |
|---|---|---|---|
| | | Equilibrated | 30 Days@140 F. |
| 16 | 0 ppm | 10 | 1 |
| 17 | 400 ppm | 10 | 10 |
| 18 | 800 ppm | 10 | 10 |
| 19 | 1200 ppm | 10 | 10 |

TABLE 3

| Sample | 4-HT Level | MFFT Initial | MFFT 10 Day@140 F. |
|---|---|---|---|
| 20 | 750 ppm | 9.5° C. | 9.5° C. |
| 21 | 1000 ppm | 7.9° C. | 10.2° C. |
| 22 | 1600 ppm | 8.3° C. | 10.9° C. |
| 23 | 2100 ppm | 9.3° C. | 10.9° C. |

Tables 2 and 3 demonstrate that levels as low as 400 ppm of 4-HT were effective at stabilizing the reactive coalescent.

EXAMPLE 3
Diafiltration of Coating Compositions

Another approach to stabilizing the DCPOEMA in coating compositions involves diafiltration of the polymer to remove residual water soluble impurities. During the diafiltration process, the aqueous phase of the polymer is replaced with clean deionized water. The coating compositions were prepared according to Paint 1 except JH-2479 was substituted for EXP-3361. The preparation of JH-2479 was as follows (materials are listed in Table 4):

A stirred reactor containing 1,283 g of deionized (D.I.) water was heated to 88° C. under nitrogen. To this was added 7.2 g of sodium carbonate dissolved in 85 g of DI water followed by a solution of 3.6 g of sodium persulfate in 20 g of DI water and 49 g (solids basis) of a 60 nm seed latex with 80.5 g of DI water. The temperature was allowed to fall to 85° C. The feed of monomer emulsion ("ME") #1 was started and fed to the reactor over 67 minutes. At the same time a feed of a solution of 1.8 g of sodium persulfate in 100 g of water was started to the reactor. The reaction temperature was held at 85° C. At the completion of the ME #1 feed the cofed sodium persulfate feed was stopped and the reaction mixture was held at temperature for 15 minutes. The ME #1 feed line was flushed to the reactor using 40 g of DI water. Then the feed of ME #2 was started and fed to the reactor over 103 minutes. The cofeed sodium persulfate feed was restarted at the start of the ME #2 feed. At the completion of both feeds the reactor was held at temperature for 30 minutes and the feed lines flushed to the reactor with 40 g of DI water. The reaction mixture was cooled to 55° C. and 0.01 g of iron sulfate heptahydrate, 0.5 g of 70% aqueous t-butyl hydroperoxide, and 0.6 g of isoascorbic acid were added in a total of 25 g of DI water. The reaction mixture was cooled to room temperature and the pH adjusted to 9.0 using ammonium hydroxide.

The final product had a solids content of 45.9%, particle size by Brookhaven BI-90 (light scattering) of 190 nm., and a Brookfield viscosity (LVT viscometer, 30 rpm, 25° C.) of 60 cps.

TABLE 4

| | ME #1 | ME #2 |
|---|---|---|
| DI water | 121.3 g | 260.0 g |
| Triton ® XN-45S | 15.8 g | 25.4 g |
| Butyl Acrylate | 326.7 g | 381.2 g |
| Methyl Methacrylate | 388.5 g | 517.3 g |
| Allyl Methacrylate | 7.3 g | |
| Methacrylic Acid | 3.6 g | 27.2 g |
| Acetoacetoxy Methacrylate | | 163.4 g |

The microfiltration unit was an Industrial Maximate manufactured by Filtron. The main feed tank was a 5 gallon polypropylene tank. The recirculating pump was an M-1 diaphragm pump manufactured by Wildon. An in-line water filter was positioned after the pump. The microfiltration membrane was an Omega series modified polyether sulfone. The molecular weight cut-off for the membrane was about 30,000. The channel size of the membrane was 40 mil. The solution being filtered was recirculated from the main feed tank to the microfiltration membrane and back to the main feed tank by the pump. A 2.5 gallon polypropylene carboy was used to collect the permeate as it was produced on the other side of the microfiltration membrane. A feed pump manufactured by Fluid Metering Pump Inc. was used to add deionized water to the main feed tank to maintain the fluid volume in the tank during filtration.

A solution was prepared by mixing 3,500 g of JH-2479 with 3,500 grams of deionized water. This solution was recirculated across the microfiltration membrane using the equipment described above. During the filtration process 10,500 g of deionized water was added to the main feed tank at a rate that equaled the rate of permeate that was collected on the other side of the microfiltration membrane. After the 10,500 g of deionized water was added and 10,500 g of permeate was collected, the solution was allowed to recirculate in the microfiltration unit until another 3,685 g of permeate was collected. The sample was drained from the unit.

The final product had a solids content of 44.2%, particle size by Brookhaven BI-90 (light scattering) of 194 nm., and a Brookfield viscosity (LVT viscometer, 30 rpm, 25° C.) of 68 cps.

Sample 24 was a control paint sample of JH2479 charged with DCPOEMA. Sample 25 was the diafiltered paint sample of JH2479 charged with DCPOEMA. Samples were stored at 140° F. for 10 days. The concentration of DCPOEMA was measured by Gas Liquid Chromatography at 0, 5, and 10 days storage. For this test, the reactive coalescent was considered stable if greater than 50% of the reactive coalescent remained after 5 and 10 days storage at 140° F. Preferred is greater than 60% of the reactive coalescent remaining after 5 and 10 days storage at 140° F. Most preferred is greater than 75% of the reactive coalescent remaining after 5 and 10 days storage at 140° F. The results are shown in Table 5.

TABLE 5

Concentration of DCPOEMA in Coating Compositions

| Sample | Polymer | Initial | 2 Week RT | 5 day @ 140 F. | 10 day @ 140 F. |
|---|---|---|---|---|---|
| 24 | JH2479 | 29,030 ppm | 28,200 ppm | 2,600 ppm | 1,365 ppm |
| 25 | Diafiltered | 28,875 ppm | 27,863 ppm | 24,982 ppm | 21,521 ppm |

The results demonstrate that diafiltration of the polymer prior to formulation with DCPOEMA improves the stability of DCPOEMA in the wet coating composition.

EXAMPLE 4

Analogs Of DCPOEMA

Sample 26—Dicyclopentenyloxyethyl Butyrate

A solution of 155.2 grams (0.8 moles) of dicyclopentenyloxyethanol and 201.5 grams (1.96 moles) of methyl butyrate was charged to a 500 ml, 3-necked flask equipped with a thermometer, a mechanical stirrer, and a 1 inch diameter-10 plate Oldershaw column fitted with a distillation head, distillate rate removal-vapor temperature controller and a graduated distillate receiver. The solution was stirred and heated to reflux (108–112° C./700 mm of Hg). The water-methyl butyrate azeotrope (18.3 g) was distilled from the reaction mixture. At the conclusion of the dehydration, the solution was cooled to 60° C. and to it was added 3.17 g (0.0056 moles) of tetraethylhexyl titanate. The reaction mixture was heated to reflux (108° C./700 mm of Hg). The methanol of reaction-methyl butyrate azeotrope was collected over a period of 4½ hours. During the reaction the reaction temperature/pressure was maintained in the range of 108–123° C./700 mm of Hg. The progress of the reaction was monitored by Gas Liquid Chromatography ("GLC") analysis of the reaction mixture, and by refractive index analysis of the methanol-methyl butyrate distillate. The reaction mixture was stripped of methyl butyrate at 72–122° C./400 mm of Hg to provide 209.5 g of orange liquid. By GLC analysis the stripped material contained 93.6% of dicyclopentenyloxyethyl butyrate.

Sample 27—Dicyclopentenyloxyethyl Acetate

A stirred reactor containing 58.1 g (0.30 moles) of dicyclopentenyloxyethanol and 200 g (2.17 moles) of toluene was heated to 41° C. A charge of 47.6 g (0.60 moles) of pyridine was added to the solution over a period of 35 minutes followed by the addition of 34.8 g (0.435 moles) of acetyl chloride over a period of 1¾ hours. During the addition of the pryidine and the acetyl chloride the reaction mixture temperature was maintained between 42–47° C. The reaction mixture was stirred and heated at 49–49.5° C. for 3¼ hours. The stirred reaction mixture was cooled to ambient temperature and to it was added 211 g of water and 100 g of toluene. The mixture was allowed to stand and the toluene layer was isolated. The toluene solution was washed with 200 ml of water, isolated, stirred with 5 g of magnesium sulfate and gravity filtered. The filtrate was stripped of toluene at reduced pressure to provide 65.4 g of yellow liquid that contained 97.2% dicyclopentenyloxyethyl acetate by GLC analysis.

Sample 28—Dicyclopentenyloxyhexanol

A stirred reactor containing 116.2 grams (0.978 moles) of 1,6-hexanediol was heated to 45° C. and sparged with nitrogen. A 3.0 gram (0.03 moles) solution of 95% sulfuric acid was added to the molten 1,6-hexanediol and the mixture was heated to 110° C. Over a period of 3½ hrs. 99.7 grams (0.76 moles) of dicyclopentadiene was fed to the reaction mixture that was stirred and heated at 110–116° C. The reaction mixture was stirred and heated for 1.5 hrs. at 115° C. and was cooled to ambient temperature. The mixture was allowed to stand at ambient temperature for several days. The mixture was stirred and to it was added 6.37 grams (0.08 moles) of 50% sodium hydroxide in water solution. The mixture was fractionally vacuum distilled to obtain two water white distillation cuts of dicyclopentenyloxy hexanol. The amounts and analysis of each cut was 56.7 grams of 88% dicyclopentenyloxyhexanol for product cut 1 and 20.5 grams of 91.5% dicyclopentenyloxyhexanol for product cut 2. The vapor temperature/vapor pressure at which the distillation cuts were isolated was 195–202° C./10–12 mm. of Hg. The distillation cuts were analyzed by GLC.

The following analogs were prepared according to the procedures described above: dicyclopentenyloxy ethyl acetate, dicyclopentenyloxy ethyl butyrate, dicyclopentenyloxy-2-(2-hydroxyethoxy)ethane, dicyclopentenyloxy-2-(2-butoxyethoxy)ethane, dicyclopentenyloxy hexanol, dicyclopentenyloxyhexane, dicyclopentenyloxybutane, dicyclopentenyloxy (2-methyl) propane, and 1,2-bis(dicyclopentenyloxy)ethane.

The analogs were tested for performance as reactive coalescents by incorporating them into coating compositions as follows:

thirty six g water, 3.21 g Tamol 165, 1.00 g Triton CF-10, 0.50 g Drew ZV-22, 7.50 g Acrysol RM-2020NPR, and 90.00 g Ti-Pure R-700 were ground on a high speed disperser for 15 minutes. The following were added with continued mixing:

257.26 g HG-95, 0.50 g Drew ZV-22, 17.94 g DCPOEMA or DCPOEMA analog, 6.21 g RM-2020NPR, and 77.83 g water. For the sample containing 1,2-bis (dicyclopentenyloxy)ethane, 35.88 g 1,2-bis (dicyclopentenyloxy)ethane was added to the sample. The samples were tested for MFFT. The results are in Table 6.

TABLE 6

| Coalescent | MFFT Initial | MFFT 10 Days @ 140 F. |
|---|---|---|
| dicyclopentenyloxy ethyl acetate | <5° C. | <5° C. |
| dicyclopentenyloxy hexanol | 5.4° C. | 3.6° C. |
| dicyclopentenyloxy ethyl butyrate | 2.9° C. | 1.6° C. |
| 1,2-bis (dicyclopentenyloxy)ethane | 4.2° C. | 3.6° C. |
| DCPOEMA | <5° C. | 23° C. |

The results indicate that the DCPOEMA analogs are more stable and therefore perform better as reactive coalescents than DCPOEMA.

EXAMPLE 5

Oligomers of DCPOEMA

Sample 29—The materials of Table 7 were combined and sparged with $N_2$. This solution was pumped through a continuous reactor at 275° C. and 3500 psi, with a flow rate such that its residence time was approximately 40 seconds. The effluent solution was stripped of solvent and residual monomer with a rotary evaporator, yielding a pale yellow oil. By GPC (in THF vs. a polyMMA standard) $M_w/M_n$=2635/2111.

TABLE 7

| material | weight (g) |
| --- | --- |
| ethyl acrylate | 42 |
| DCPOEMA | 50 |
| acrylic acid | 8 |
| acetone | 300 |
| di t-butyl peroxide | 1 |

Sample 30—The reactive coalescent sample was prepared by adding 2.76 grams of aqueous ammonia (28%) to 40.00 grams of Sample 29. This modifed material was used as the reactive coalescent in the following formulation: 18.00 g water, 1.61 g Tamol®165, 0.50 g Triton®CF-10, 0.25 g Drew®ZV-22, 3.75 g RM-2020NPR, and 45 g Ti-Pure®R-706 were ground with a high speed disperser for 15 minutes. To this was added with continued stirring: 131.27 g EXP-3361, 16.14 g reactive oligomer, 0.25 g Drew®ZV-22, 10.50 g RM2020NPR, and 40.25 g water. The samples were tested for MFFT. The results are in Table 8.

TABLE 8

| | MFFT | |
| --- | --- | --- |
| Coalescent | Equilibrated | 10 days @ 140 F. |
| DCPOEMA | 5.3° C. | >18° C. |
| Sample 30 (oligomer) | 2.7° C. | 3.9° C. |

The results indicate that the DCPOEMA containing oligomers are more stable and therefore perform better as reactive coalescents than DCPOEMA.

We claim:

1. A process for the preparation of polymers comprising the steps of:
   a) providing a compound selected from the group consisting of dicyclopentenyloxy acrylate, dicyclopentenyloxy methacrylate, dicyclopentenyloxyethyl acrylate, and dicyclopentyloxyethyl methacrylate;
   b) providing a solvent selected from the group consisting of water, acetone, methanol, isopropanol, propionic acid, acetic acid, toluene, hexane, ethyl acetate, methylethyl ketone, dimethyl formamide, dimethylsulfoxide, and combinations thereof,
   c) providing an initiator;
   d) forming a reaction mixture by admixing the solvent, the initiator, and the compound selected from the group consisting of dicyclopentenyloxy acrylate, dicyclopentenyloxy methacrylate, dicyclopentenyloxyethyl acrylate, and dicyclopentyloxyethyl methacrylate; and
   e) passing the reaction mixture through a heated zone wherein the reaction mixture is maintained at a temperature of at least 175° C. for from 0.1 seconds to 300 seconds to form a liquid polymer with a number average molecular weight of from 450 to 10,000.

2. The process according to claim 1 wherein the reaction mixture further comprises a compatible monomer selected from the group consisting of methyl acrylate, ethyl acrylate, butyl acrylate, t-butylaminoethyl methacrylate, dimethylaminoethyl methacrylate, isobornyl methacrylate, styrene, vinyl toluene, methacrylic acid, methyl methacrylate, butyl methacrylate, isobutyl methacrylate, allyl methacrylate, lauryl methacrylate, and 2-ethylhexyl methacrylate.

3. The process according to claim 1 wherein the reaction mixture is maintained at a temperature in the range of 225° C. to 450° C.

4. The process according to claim 1 wherein the reaction mixture is polymerized at a pressure in the range of from 1,000 to 5,000 pounds per square inch.

5. The process according to claim 1 wherein the liquid polymer has a number average molecular weight in the range of from 450 to 5,000.

6. The process according to claim 5 wherein the liquid polymer has a number average molecular weight in the range of from 450 to 3,000.

* * * * *